US011944661B2

(12) United States Patent
Choi et al.

(10) Patent No.: US 11,944,661 B2
(45) Date of Patent: Apr. 2, 2024

(54) **PHARMACEUTICAL COMPOSITION CONTAINING EXTRACT OF LEAVES OF *VACCINIUM bRACTEATUM* THUNB. FOR PREVENTION OR TREATMENT OF STRESS DISEASE AND DEPRESSION**

(71) Applicant: JEONNAM BIOINDUSTRY FOUNDATION, Jeollanam-do (KR)

(72) Inventors: Chul Yung Choi, Gwangju (KR); Dool Ri Oh, Jeollanam-do (KR); Yu Jin Kim, Jeollanam-do (KR); Eun Jin Choi, Jeollanam-do (KR); Hyun Mi Lee, Gwangju (KR); Dong Hyuck Bae, Jeollanam-do (KR); Kyo Nyeo Oh, Gwangju (KR); Myung-A Jung, Jeollanam-do (KR); Ji Ae Hong, Jeollanam-do (KR); Kwang Su Kim, Jeollanam-do (KR); Hu Won Kang, Gwangju (KR); Jae Yong Kim, Jeollanam-do (KR); Sang O Pan, Gwangju (KR); Sung Yoon Park, Jeollanam-do (KR); Rack Seon Seong, Jeollanam-do (KR)

(73) Assignee: JEONNAM BIOINDUSTRY FOUNDATION, Jeollanam-do (KR)

( * ) Notice: Subject to any disclaimer, the term of this patent is extended or adjusted under 35 U.S.C. 154(b) by 144 days.

(21) Appl. No.: 16/618,505

(22) PCT Filed: Feb. 7, 2018

(86) PCT No.: PCT/KR2018/001647
§ 371 (c)(1),
(2) Date: Dec. 2, 2019

(87) PCT Pub. No.: WO2018/221835
PCT Pub. Date: Dec. 6, 2018

(65) Prior Publication Data
US 2020/0121749 A1 Apr. 23, 2020

(30) Foreign Application Priority Data
Jun. 1, 2017 (KR) .................. 10-2017-0068604

(51) Int. Cl.
*A61K 36/45* (2006.01)
*A61P 25/22* (2006.01)
*A61P 25/24* (2006.01)

(52) U.S. Cl.
CPC .............. *A61K 36/45* (2013.01); *A61P 25/22* (2018.01); *A61P 25/24* (2018.01)

(58) Field of Classification Search
CPC .................................................. A61K 36/45
See application file for complete search history.

(56) References Cited

FOREIGN PATENT DOCUMENTS

| CN | 105748666 A | * | 7/2016 |
| KR | 10-2016-0025414 A | | 3/2016 |
| KR | 10-2016-0119347 A | | 10/2016 |

OTHER PUBLICATIONS

CN-105748666-A translated doc (Year: 2016).*
Lam (A Review on Medicinal Properties of Orinetin, Hindawi Publishing Corp, Advances in Pharm. Scien., vol. 2016, Article ID 4104595). (Year: 2016).*
Ebenezer (The Anti-Inflammatory Effects of Blueberries in an Animal Model of Post-Traumatic Stress Disorder (PTSD) (, PLoS ONE 11(9) Sep. 7, 2016). (Year: 2016).*
Beutel (Noise Annoyance Is Associated with Depression and Anxiety in the General Populaion—The Contribution of Aircraft Noise, PLOS ONE, May 19, 2016) (Year: 2016).*
Chiba (Chronic restraint stress causes anxiety- and depression-like behaviors, down regulates glucocorticoid receptor expression, and attenuates glutamate release induced by brain-derived neurotrophic factor in the prefrontal cortex, Prog. in Neuro Psychopharm. & Biological Psychiatry 39 (2012) 112-119.*
Eesr of european patent application No. 18809112.8 issued on Feb. 27, 2020.
Office action of european patent application No. 18809112.8 dated Jan. 28, 2021.
Office action of chinese patent application No. 201880035664.8 dated Apr. 28, 2021.
Oh, dool-ri, et al.; "*Vaccinium bracteatum* leaf extract reverses chronic restraint stress-induced depression-like behavior in mice: regulation of hypothalamic-pituitary-adrenal axis, seratonin turnover systems, and erk/akt phosphorylation", fronteirs in pharmacology, Jul. 2019, vol. 9, article 604, pp. 1-16.
Wang, I., et al.; "effect of *Vaccinium bracteatum* thunb. leaves extract on blood glucose and plasma lipid levels in streptozotocin-induced diabetic mice", journal of ethnopharmacology 130 (2010) 465-469.
Hu, j., et al.; "phytochemical compositions, antioxidant and antimicrobial activities analysis of extracts from *Vaccinium bracteatum* thunb. leaves", journal of applied botany and food quality 89, 150-155 (2016).
Wang, s., et al.; (2016). protective effect of the orientin on noise-induced cognitive impairments in mice. behavioural brain research, 296 290-300.

(Continued)

*Primary Examiner* — Terry A McKelvey
*Assistant Examiner* — Jacob A Boeckelman
(74) *Attorney, Agent, or Firm* — Harness, Dickey & Pierce, P.L.C.

(57) ABSTRACT

The present invention provides a pharmaceutical composition for prevention or treatment of a stress disease and depression, the pharmaceutical composition be safely useable without toxicity and side effects by using an extract of leaves of *Vaccinium bracteatum* Thunb., which is natural resource of Korea, so that the reduction of manufacturing and production costs and the import substitution and export effects can be expected through the replacement of a raw material for preparation with a plant inhabiting in nature.

3 Claims, 18 Drawing Sheets

(56) References Cited

OTHER PUBLICATIONS

Bouayed, j., et al.; "oxidative stress and anxiety", oxidative medicine and cellular longevity, 2:2, pp. 63-67, 2009.
Zhou sannv et al, "advance on study of leaves of *Vaccinium bracteatum* thunb.", the light & textile industry of fujian No. 8, p. 37-41.
Liu jian xiang et al, "synergic antidegressive effect of quercetin and hypericum perforatum extract in mice", journal of zhejiang university (medical sciences), vol. 42, No. 6, pp. 615-619.
Liu yi et al, "effect of luteolin on depression in mice caused by chronic unpredictable mild stress", lishizhen medicine and materia medica research, vol. 24, No. 6, pp. 1382-1384.
Lij, Y et al., "Orientin Improves Depression-like Behavior and BDNF in Chronic Stressed Mice", Mol Nutr. Food Res., 2015, vol. 59, pp. 1130-1142.
Zhang. J. et al., "Isolation and Identification of Antioxidant Compounds in Vaccinium Bracteatum Thunb. by UHPLC-Q-TOF LC/MS and Their Kidney Damage Protection", Journal of Functional Foods, 2014, vol. 11, pp. 62-70.
Lee, W. et al., "Antithrombotic and Antiplatelet Activities of Orientin in Vitro and in Vivo", Journal of Functional Foods, 2015, vol. 17, pp. 388-398.
International Search Report from corresponding PCT Application No. PCT/KR2018/001647, dated Jun. 1, 2018.

\* cited by examiner

PHARMACEUTICAL COMPOSITION CONTAINING EXTRACT OF LEAVES OF *VACCINIUM bRACTEATUM* THUNB. FOR PREVENTION OR TREATMENT OF STRESS DISEASE AND DEPRESSION

CROSS-REFERENCE TO RELATED APPLICATIONS

This application is a national phase application of PCT Application No. PCT/KR2018/001647 filed on Feb. 7, 2018, which claims priority to Korean Patent Application No. 10-2017-0068604 filed on Jun. 1, 2017. The entire disclosures of the applications identified in this paragraph are incorporated herein by reference.

FIELD

The present invention relates to a pharmaceutical composition comprising a *Vaccinium bracteatum* Thunb. leaf extract as an effective ingredient for prevention or treatment of stress-related disease and depression and, more particularly, to a pharmaceutical composition for prevention or treatment of stress-related disease and depression, which employs a *Vaccinium bracteatum* Thunb. leaf extract, which is a natural material, and can be safely used with neither toxicity nor side effects.

BACKGROUND

When combined with a lack of coping resources available or used by an individual, stress can often lead to the development of psychological issues characterized by significant feelings of anxiety, depression, and nervousness or physical issues such as decreased appetite.

Depression is a mood disorder that causes various cognitive and psychosomatic symptoms characterized mainly by persistent feelings of sadness and loss of interest, leading to aversion to activity in daily life. Depressive disorder is a serious illness that causes a change in feeling, thought, physical condition, and behavior, affecting an individual's overall life. Depression is different from a temporary feeling of sadness and is neither an expression of personal weakness nor can be eliminated by personal will.

Depressive disorder is one of the most common mental illnesses, and the prevalence significantly differs from one country to another.

The percentage of people who are affected by major depressive disorder at one point in their life accounts for as high as 10.1%-16.6% in the United States, Europe, and New Zealand, but decreases to 5% or less in non-Western countries including Korea and China.

As of 2011, the Korean Department of Health and Welfare's Epidemiological Survey of Mental Illness showed that Korean people were affected with major depressive disorder for their lives at a lifetime prevalence of 6.7%, with the one-year prevalence accounting for 3.1%, which have become higher than those measured in the epidemiological studies in 2006, but remained lower than those in Western countries. The lifetime and one-year prevalence were similar to or somewhat higher than those in non-Western countries. The apparent cause of depression is not yet clear, but a variety of biochemical, genetic, and environmental factors could cause depression, like other mental illnesses. Unlike other diseases, depression can be expected to be cured in its advanced stage if it is appropriately treated by a specialist whereby the patients can return to their normal lives.

*Vaccinium bracteatum* Thunb. is a dicotyledon angiosperm plant in the order of Ericales and grows to 1-3 meters in mountainous areas by the seashore. Its small branches are grayish brown to gray and are almost hairless. The leaves are of alternate phyllotaxis, thick, and elliptical or long oval, with a thick leather-like texture. There are small sawteeth on the edge and small pellucid dots below the backside of the leaves. The plant gives bloom in June to 10 reddish white flowers at the raceme dropping downward, with bracts remaining. The fruits are round and edible berries covered with white powder and mature to a diameter of 6 mm in October.

Recently, as the living standards of modern people have improved, there has been a growing interest in natural resources that have little side effects and can be harvested from nature. In particular, studies have been actively made on health foods containing natural functional substances that contain nutrients necessary for the human body or specifically for prevention of and rehabilitation from diseases. *Vaccinium bracteatum* Thunb. is also investigated for functions, but there is yet a lack of information on nutritional values and physiological activities thereof.

SUMMARY

Technical Problem

The present disclosure aims to provide a use of the natural resource *Vaccinium bracteatum* Thunb., of which the physiological activity has remained unclear, in a functional food composition and a pharmaceutical composition. In this context, the present disclosure provides a pharmaceutical composition comprising a *Vaccinium bracteatum* Thunb. leaf extract as an effective ingredient for prevention or treatment of stress-related disease and depression, which can be safely used with neither toxicity nor side effects.

Technical Solution

The present disclosure provides a pharmaceutical composition for prevention or treatment of stress-related disease and depression, which employs an extract from the natural resource *Vaccinium bracteatum* Thunb. leaves and can be safely used without toxicity and side effects.

For use in a pharmaceutical composition and a functional food composition for prevention or treatment of stress-related disease and depression, an extract was obtained by adding 400 g of *Vaccinium bracteatum* Thunb. leaves to 8 L of distilled water, heating the mixture to 100° C. and maintaining the same temperature for 3 hours by means of a reflux extractor, vacuum filtering the resulting extract, and concentrating the filtrate at a reduced pressure to afford 31.52 g of the concentrate.

Provided is also a pharmaceutical composition for prevention or treatment of stress-related disease or depression, in which an extract dissolved in water, methanol, ethanol, propanol, isopropanol, butanol, or a mixture solvent thereof is contained as an effective ingredient in an amount of 0.01 to 99.9 wt. %. The composition may be prepared in the form of one selected from a tablet, a capsule, a soft capsule, a granule, a liquid agent, or a beverage.

Advantageous Effect

The *Vaccinium bracteatum* Thunb. leaf extracts according to the present disclosure were found to have an excellent anti-depressive effect as proven by reducing the immobility time during which the limbs do not move at all, with the superiority of hot-water extracts to 80% methanol extracts. Thus, the *Vaccinium bracteatum* Thunb. leaf extracts can be used for a pharmaceutical composition for prevention or treatment of stress-related disease and depression. In addition, by employing the plant inhabiting in nature as a raw material, the present disclosure can reduce the production cost and is expected for import substitution and export effects through industrialization.

DETAILED DESCRIPTION

1. Preparation of Hot Water Extract of *Vaccinium bracteatum* Thunb. Leaf

To 8 L of distilled water were added 400 g of *Vaccinium bracteatum* Thunb. leaves which were then to 100° C. and extracted for 3 hours at the temperature using a reflux extractor. The resulting extract was vacuum filtered and vacuum concentrated to obtain 31.52 g of a concentrate.

2. Preparation of 80% Methanol Extract of *Vaccinium bracteatum* Thunb Leaf

Twenty grams of the *Vaccinium bracteatum* Thunb. leaves were added to 20 L of 80% methanol, heated to 100° C. and extracted for 3 hours at the temperature using a reflux condenser. The resulting extract was vacuum filtered and then vacuum concentrated to obtain 6.99 g of a concentrate.

3. Experimental Animals and Breeding

For use in assaying an antidepressant effect of the *Vaccinium bracteatum* Thunb. leaf extracts, male ICR mice, 6 weeks of age, were purchased from SAMTACO, Korea. The animals were acclimated to a certain condition in an animal breeding room (temperature: 22±2° C., humidity: 50±5%, contrast: 12-hour light/12-hour dark cycle) for one week before use.

4. Anti-Depressive Animal Behavior Test Using *Vaccinium bracteatum* Thunb. Leaf Extract in Normal Mouse Male ICR mice were orally administered the *Vaccinium bracteatum* Thunb. leaf extract the present invention while escitalopram oxalate was used as an antidepressant for a comparative group. Oral administration was conducted for 1 or 6 days according to the experiment.

In a forced swimming test (FST), which is a pre-swim test on the day before the main test (post-swim), tap water of around 25° C. was poured into a cylindrical water tank (about 20 cm in diameter, 40 cm in height) to the height of 15 cm from the bottom, after which the mice were put thereinto and forced to swim for 15 minutes. Then, the mice were withdrawn from the water, wiped with a dry towel, and returned to the breeding box. After 1 or 6 days of drug administration, the main test (post-swim) was performed and video was taken with forced swimming for 6 minutes with the mice in the cylinder. In the recorded images for the five minutes exclusive of the first one minute, the animal behavior was classified into three types for analysis: the animals were floating in the water, showing a slight movement, with only a part of the upper body including the face exposed on the water face (immobility behavior); the animals were swimming around the cylinder in the horizontal direction while splashing the water with their forepaws and rear paws (swimming behavior); and the animals were making the fierce movement of pulling the paws out of the water, scrapping the wall (climbing behavior). Times for the three movements were measured.

Figure 1:
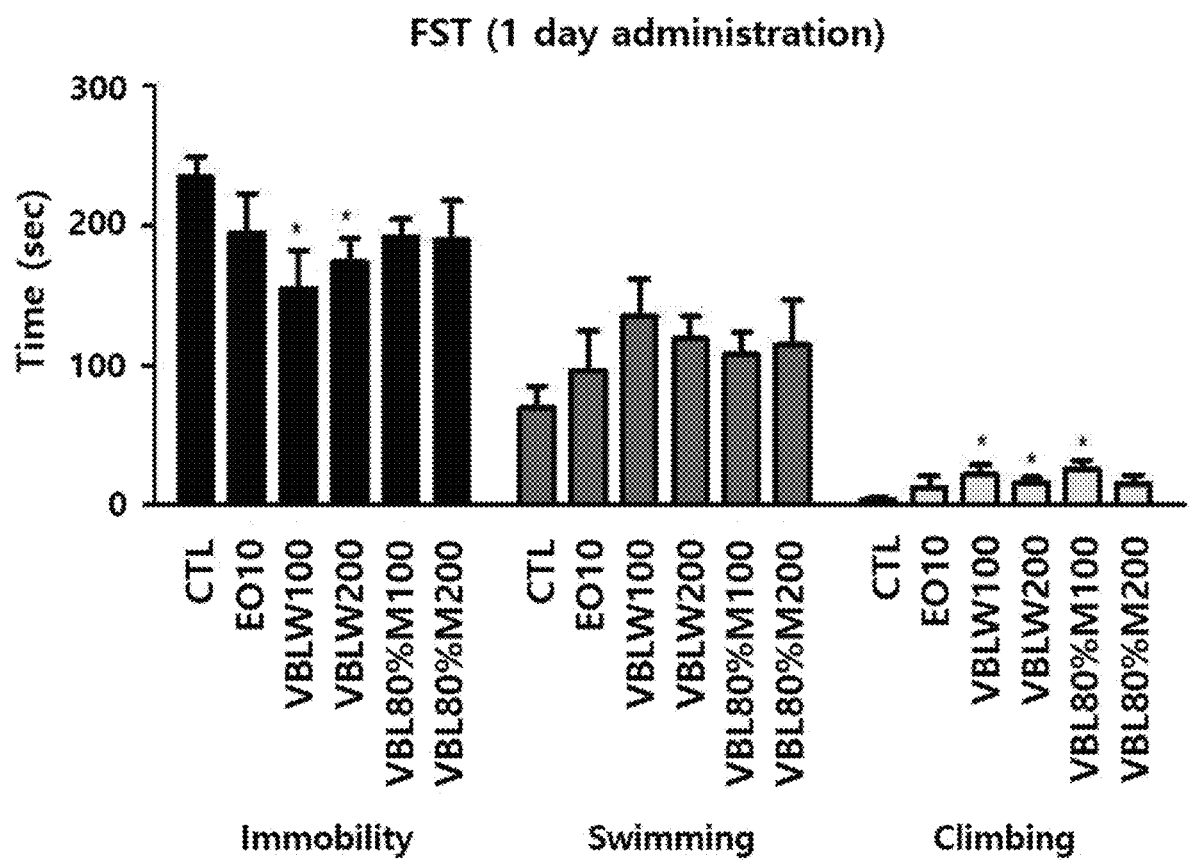
FIG. 1 is a graph showing immobility times, swimming times, and climbing times in the forced swimming test for mice to which *Vaccinium bracteatum* Thunb. leaf extracts of the present disclosure were administered for one day, in comparison with escitalopram oxalate-administered mice as a control.

FIG. 1 shows immobility times, swimming times, and climbing times in the forced swimming test for mice to which *Vaccinium bracteatum* Thunb. leaf extracts of the present disclosure were administered for one day, in comparison with escitalopram oxalate-administered mice as a control. As shown in FIG. 1, the immobility time in the forced swimming after one-day administration of each drug was 234.59±5.95 seconds for the control, 194.65±11.55 seconds for the comparative group escitalopram oxalate, 155.14±11.14 and 173.78±6.95 seconds for hot water extracts of *Vaccinium bracteatum* Thunb. leaves (VBLW 100 and 200 mg/kg p.o), respectively, and 191.83±5.21 and 189.81±11.41 seconds for 80% methanol extracts of *Vaccinium bracteatum* Thunb. leaves (VBL80% M 100 and 200 mg/kg p.o), respectively, with a significant reduction for the groups to which the hot-water extracts of *Vaccinium bracteatum* Thunb. leaves were administered (P<0.05). Compared to the control (3.34±0.88 seconds), the climbing time was significantly increased to 12.43±3.47 seconds in the comparative group of escitalopram oxalate, to 21.50±3.02 and 15.87±1.72 seconds in the respective groups of hot water extracts of *Vaccinium bracteatum* Thunb. leaves (100 and 200 mg/kg p.o), and to 25.45±2.64 and 15.22±2.4 second in the respective groups of 80% methanol extracts of *Vaccinium bracteatum* Thunb. leaves (100 and 200 mg/kg p.o) (P<0.05).

Figure 2:
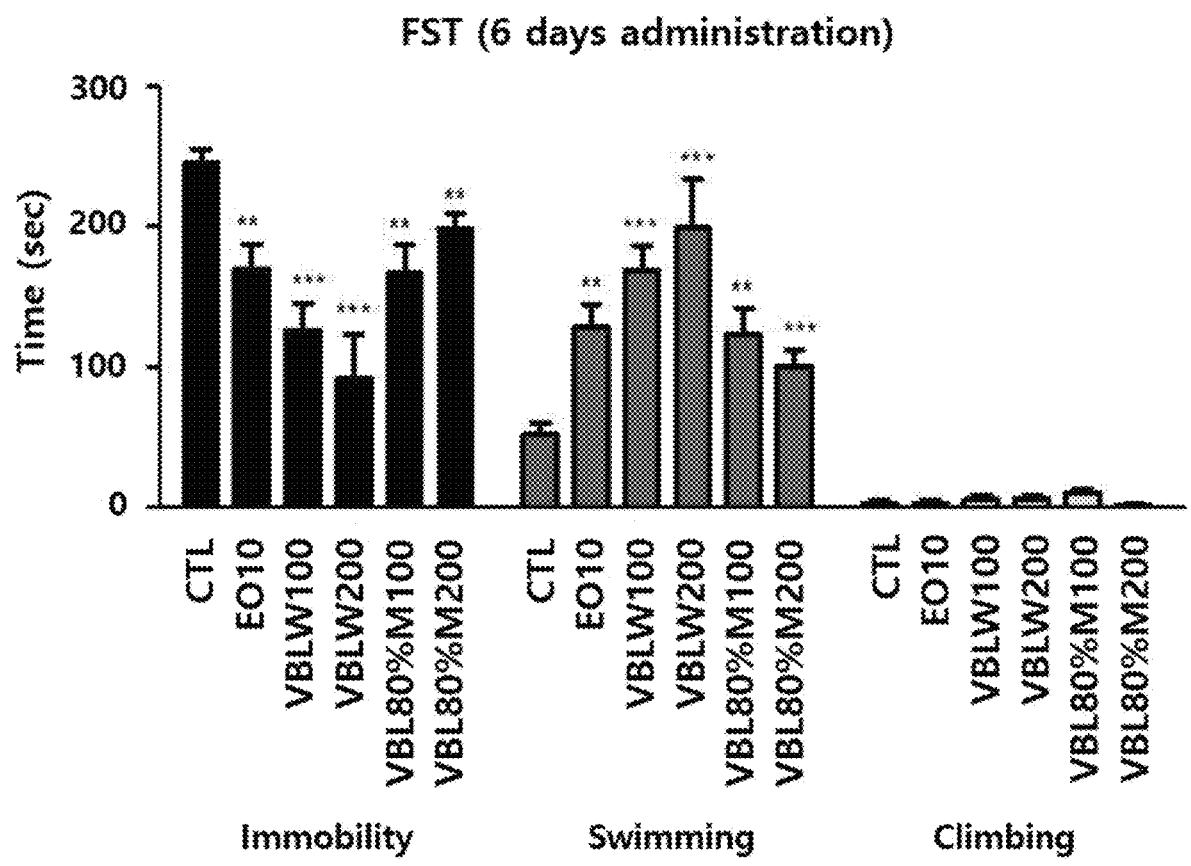
FIG. 2 is a graph showing immobility times, swimming times, and climbing times in the forced swimming test for mice to which *Vaccinium bracteatum* Thunb. leaf extracts of the present disclosure were administered for six days, in comparison with escitalopram oxalate-administered mice as a control.

FIG. 2 shows immobility times, swimming times, and climbing times in the forced swimming test for mice to which *Vaccinium bracteatum* Thunb. leaf extracts of the present disclosure were administered for six days, in comparison with escitalopram oxalate-administered mice as a control. As shown in FIG. 2, the immobility time in the forced swimming after six-day administration of each drug was 245.48±4.05 seconds for the control, 169.65±7.15 seconds for the comparative group escitalopram oxalate, 125.85±7.90 and 91.66±12.86 seconds for hot water extracts of *Vaccinium bracteatum* Thunb. leaves (VBLW 100 and 200 mg/kg p.o), respectively, and 166.34±8.36 and 198.01±4.73 seconds for 80% methanol extracts of *Vaccinium bracteatum* Thunb. leaves (VBL80% M 100 and 200 mg/kg p.o), respectively, with a significant reduction for the *Vaccinium bracteatum* Thunb. leaf extracts (P<0.01 and P<0.001).

Compared to the control (51.82±3.38 seconds), the swimming time was significantly increased to 128.16±6.65 seconds in the comparative group of escitalopram oxalate, to 168.56±7.28 and 198.95±14.33 seconds in the respective groups of hot water extracts of *Vaccinium bracteatum* Thunb. leaves (100 and 200 mg/kg p.o), and to 123.06±7.69 and 100.71±4.68 second in the respective groups of 80% methanol extracts of *Vaccinium bracteatum* Thunb. leaves (100 and 200 mg/kg p.o) (P<0.01 and P<0.001).

As described above, the *Vaccinium bracteatum* Thunb. leaf extracts of the present invention exhibited an excellent antidepressant effect because they reduced the immobility time during which the animals did not move their limbs at all, with the superiority of the hot water extract to the 80% methanol extract.

5. Serum Stress Hormone Corticosterone Level in *Vaccinium bracteatum* Thunb. Leaf Extract-Administered Normal Mouse After six days of drug administration to mice in a normal state, effects on the level of the stress hormone corticosterone in sera of the mice were measured using the Abnova ELISA kit according to the manufacturer's instruction.

Figure 3:
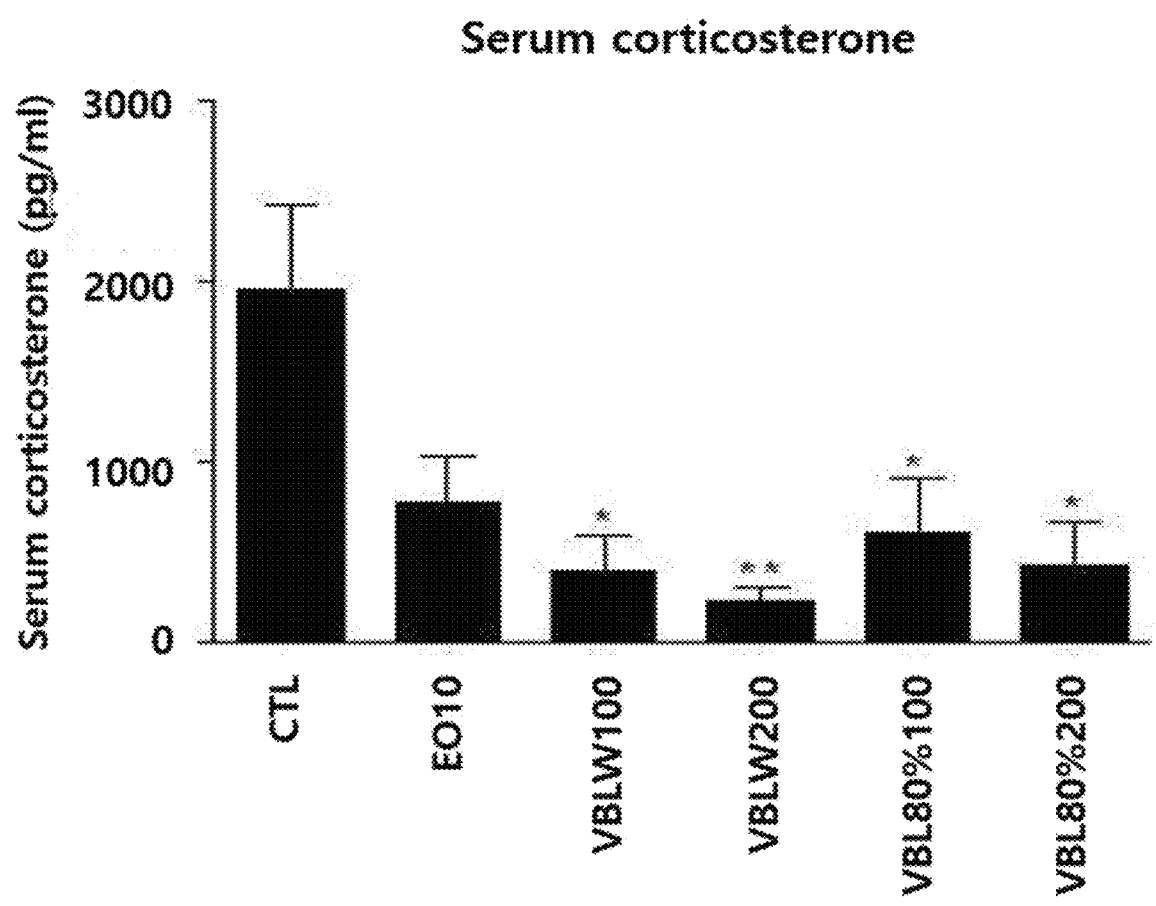
FIG. 3 is a graph showing measured levels of the stress hormone in sera of mice to which the *Vaccinium bracteatum* Thunb. leaf extracts of the present disclosure were administered, in comparison with escitalopram oxalate-administered mice as a control.

FIG. 3 show measured levels of the stress hormone corticosterone in sera of mice to which the *Vaccinium bracteatum* Thunb. leaf extracts were administered. As shown in FIG. 3, the stress hormone corticosterone was measured to be 1943.10±175.29 μg/ml for the control, 764.57±97.50 μg/ml for the comparative group of escitalopram oxalate, 396.22±75.73 μg/ml and 218.26±34.16 μg/ml, for hot-water extracts of *Vaccinium bracteatum* Thunb. leaves (VBLW 100 and 200 mg/kg p.o), respectively, and 608.10±121.11 μg/ml and 420.92±99.83 μg/ml for 80% methanol extracts of *Vaccinium bracteatum* Thunb. leaves (VBL80% M 100 and 200 mg/kg p.o), respectively, with a significant reduction for the hot-water extracts of *Vaccinium bracteatum* Thunb. leaves (P<0.05 and P<0.01).

As described above, the *Vaccinium bracteatum* Thunb. leaf extracts of the present disclosure significantly reduce the stress-induced corticosterone secretion as proven by the reduced levels of the stress hormone in sera of the *Vaccinium bracteatum* Thunb. leaf extract-administered animals after the forced swimming.

6. Anti-Depressive Animal Behavior Test using *Vaccinium bracteatum* Thunb. Leaf Extract under Chronic Restraint Stress (CRS)

Male ICR mice were purchased and subjected to chronic restraint stress (CRS). In this regard, a constant restraint stress was given by immobilizing the mice for 6 hours per day (a.m. 11 to p.m.5) in an acrylic box 20 cm in height and 7 cm in diameter for three weeks. The hot-water extracts of *Vaccinium bracteatum* Thunb. leaves were orally administered at each dose to the mice daily 30 min before the stress was given at the same time. For the control, the same volume of saline was administered. As a comparative group, escitalopram oxalate, which is an antidepressant, was orally administered. Animal behavior tests were performed the next day after 3 weeks of restraint stress stimulation. The open field test (OFT) was followed by the forced swimming test (FST). After the FST evaluation, whole blood was collected from the mice which were then autopsied to excise the hippocampus and prefrontal cortex. These brain tissues were immediately stored at −70° C. until use in experiments.

Figure 4:
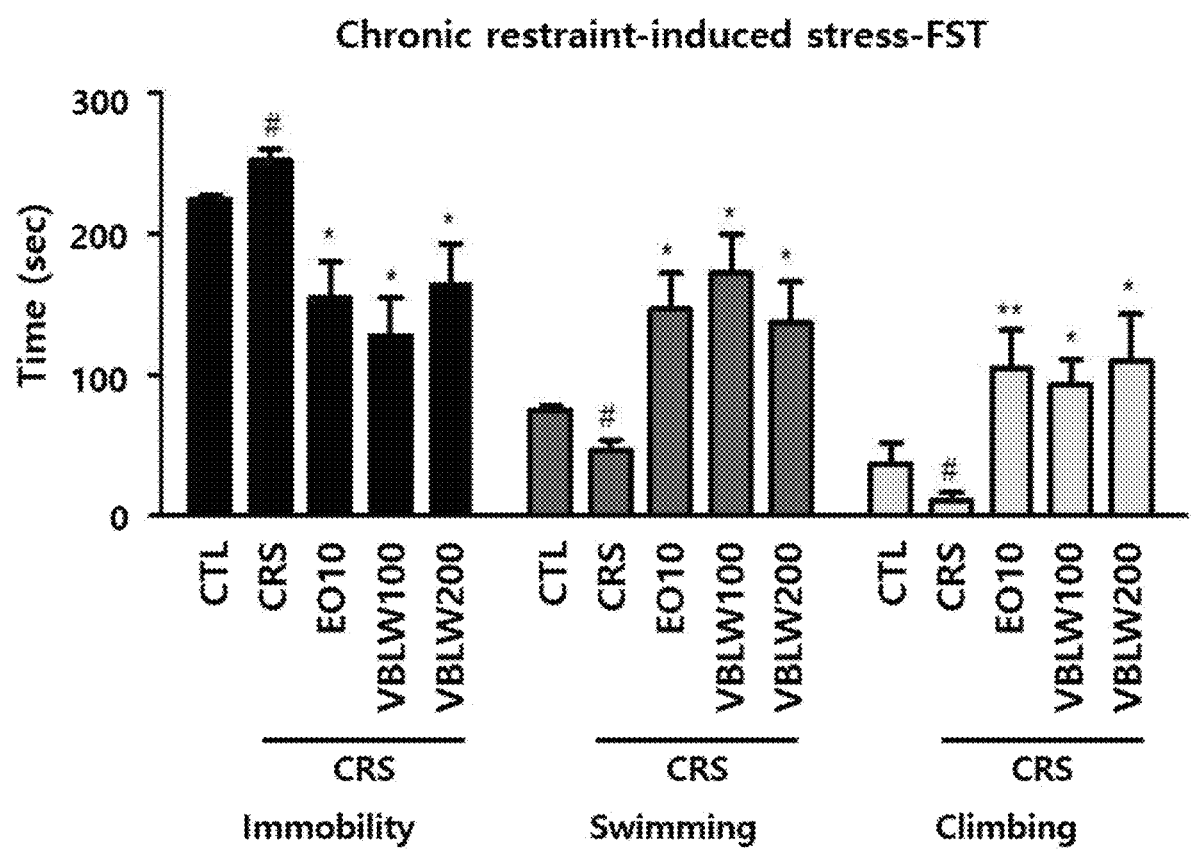
FIG. 4 is a graph showing effects of the *Vaccinium bracteatum* Thunb. leaf extracts of the present disclosure on chronic restraint stress induced in mice as assayed by forced swimming test (FST).

FIG. 4 shows effects of the *Vaccinium bracteatum* Thunb. leaf extracts of the present disclosure on chronic restraint stress in mice as assayed by forced swimming test (FST). As shown in FIG. 4, when FST was performed the next day after the mice were treated with each drug following three weeks of CRS, the immobility time was 224.22±1.99 seconds for the control, 252.29±4.67 for the chronic restraint stress group (CRS), 154.74±14.80 seconds for the positive control group of escitalopram oxalate (EO 10 mg/kg p.o), and 127.81±18.28 and 183.49±15.27 seconds for hot water extracts of *Vaccinium bracteatum* Thunb. leaves (VBLW 100 and 200 mg/kg p.o), respectively, with a significant reduction for the groups to which the hot-water extracts of *Vaccinium bracteatum* Thunb. leaves were administered (P<0.05). Compared to the control (74.95±1.90 seconds), the swimming time was significantly increased to 46.67±4.29 seconds in the chronic restraint stress group, to 146.58±14.84 seconds to in the positive control group of escitalopram oxalate, and 172.40±18.31 and 116.91±15.11 seconds in the respective groups of hot water extracts of *Vaccinium bracteatum* Thunb. leaves (100 and 200 mg/kg p.o) (P<0.05). In addition, the climbing time was measured to be 10.43±3.37 seconds in the chronic restraint stress group, 105.23±15.37 seconds in the positive control group of escitalopram oxalate, and 92.93±11.98 and 79.50±20.75 seconds in the respective *Vaccinium bracteatum* Thunb. leaf hot-water extract-administered groups (VBLW 100 and 200 mg/kg p.o), with significant increases compared to the control (37.06±8.90 seconds) (P<0.05).

The open field test (OFT) is an experimental test used to assay locomotor activity levels of animals to determine the anti-anxiety and anti-depressive effects of drugs. An OFT box is an arena having the dimensions of 60 cm diameter×20 cm height with the bottom surface divided into 25 cells. Experimental animals were individually introduced into the OFT box per test. In the OFT box, the number of cells which the animal voluntarily crossed for 5 minutes was counted. Locomotor activity was compared between groups by using the mean values thereof.

Figure 5:
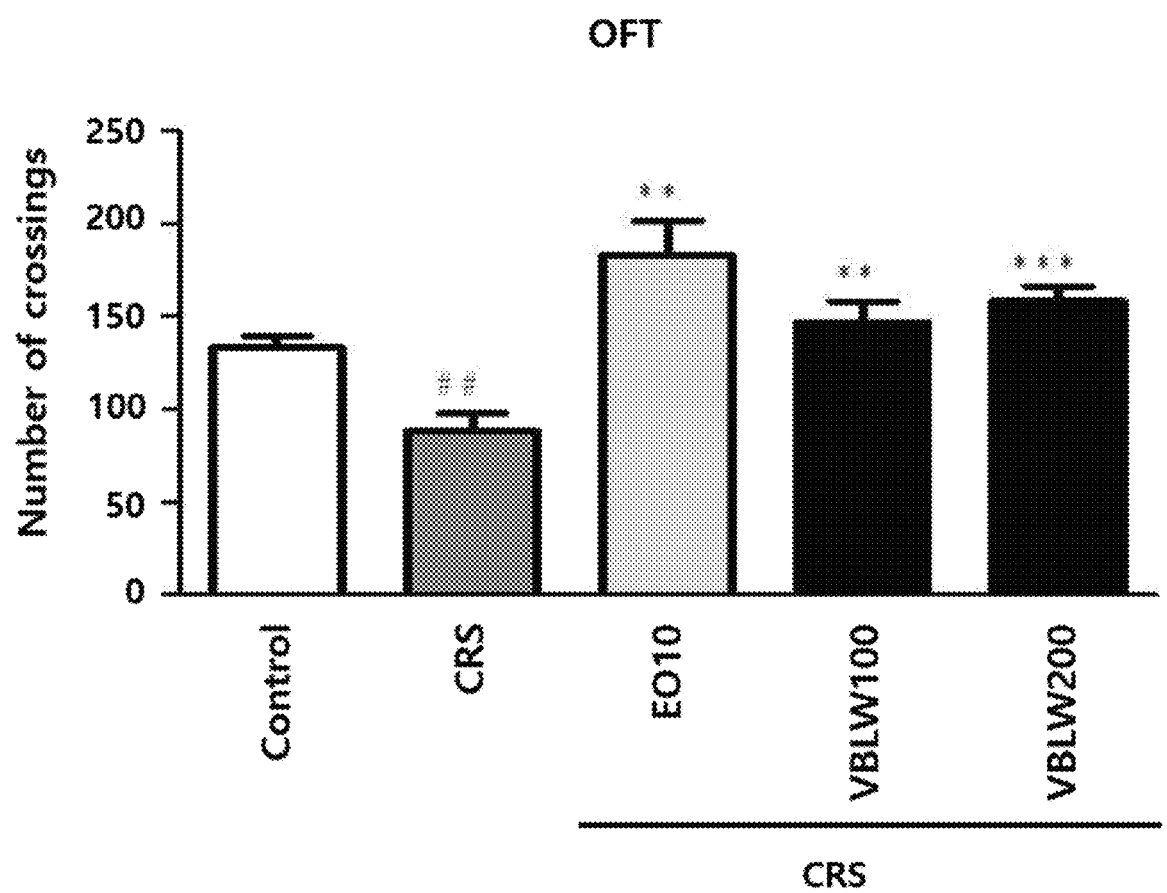
FIG. 5 is a graph showing effects of the *Vaccinium bracteatum* Thunb. leaf extracts of the present disclosure on chronic restraint stress induced in mice as measured by the open field test (OFT).

FIG. 5 shows effects of the *Vaccinium bracteatum* Thunb. leaf extracts of the present disclosure on chronic restraint stress induced in mice as measured by the open field test (OFT). As shown in FIG. 5, the number of crossing was reduced in the chronic restraint stress group (CRS, 88.00±4.82 crossings), compared to the control (133.09±1.86 crossings). In contrast, the locomotor activity was increased in the positive control of escitalopram oxalate and the *Vaccinium bracteatum* Thunb. leaf hot-water extract-administered groups (VBLW 100 and 200 mg/kg p.o), as demonstrated by the data of 182.73±5.60 crossings, 147.00±3.64 crossings, and 158.22±2.64 crossings therefor, respectively, compared to the CRS group ($P<0.01$ and $P<0.001$).

7. Levels of Stress Hormone in Serum and Neurotransmitter in Hippocampus and Prefrontal Cortex in *Vaccinium bracteatum* Thunb. Leaf Extract-Administered Animal under Chronic Restraint Stress (CRS)

On the next day after drug administration subsequent to the three weeks of chronic restraint stress, levels of the stress related hormone corticosterone in sera and the neurotransmitters (serotonin, dopamine, and norepinephrine) in the hippocam pus and the prefrontal cortex were examined.

Figure 6:
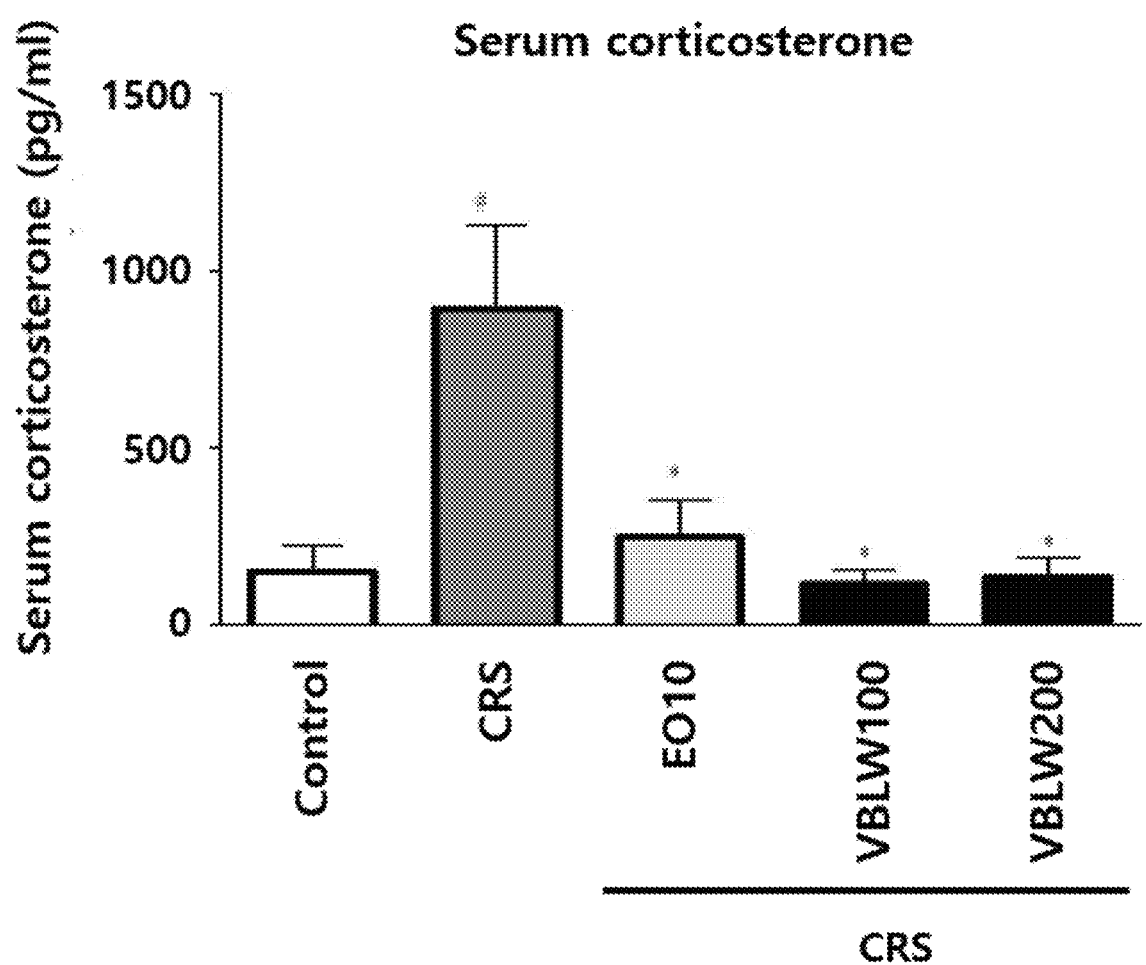
FIG. 6 is a graph showing effects of the *Vaccinium bracteatum* Thunb. leaf extracts of the present disclosure on stress hormone levels induced in mice having chronic restraint stress induced therein.

As shown in FIG. 6, serum corticosterone levels were significantly increased in the chronic restraint stress group (CRS), compared to the control (CTL) ($P<0.05$) and significantly reduced in the *Vaccinium bracteatum* Thunb. leaf hot-water extract-administered groups (VBLW 100 and 300 mg/kg p.o), compared with the chronic restraint stress group ($P<0.05$).

Figure 7A:
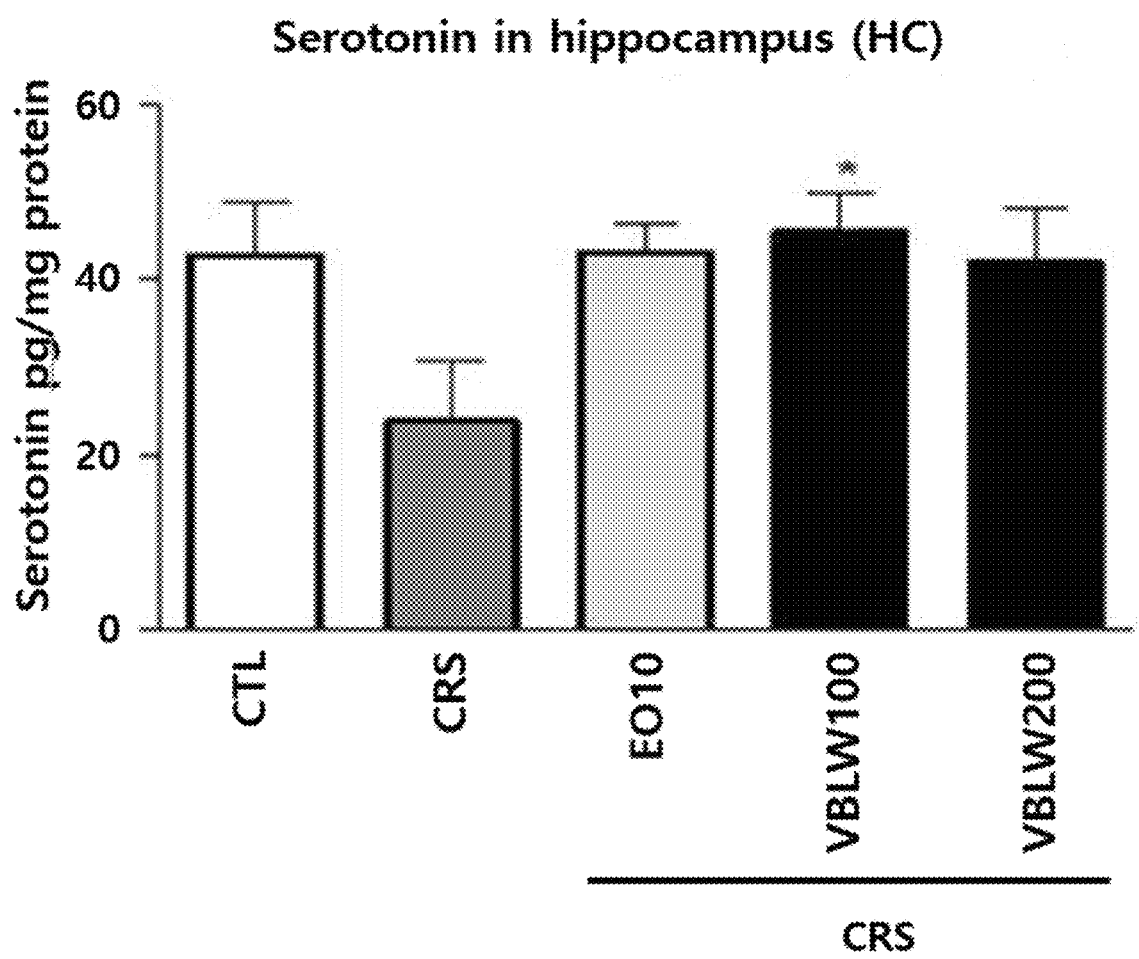
FIGS. 7A, 7B and 7C show effects of the *Vaccinium bracteatum* Thunb. leaf extracts of the present disclosure on levels of the neurotransmitters serotonin, norepinephrine, and dopamine in the hippocampus (HC) of mice having chronic restraint stress induced therein.
Figure 7B:
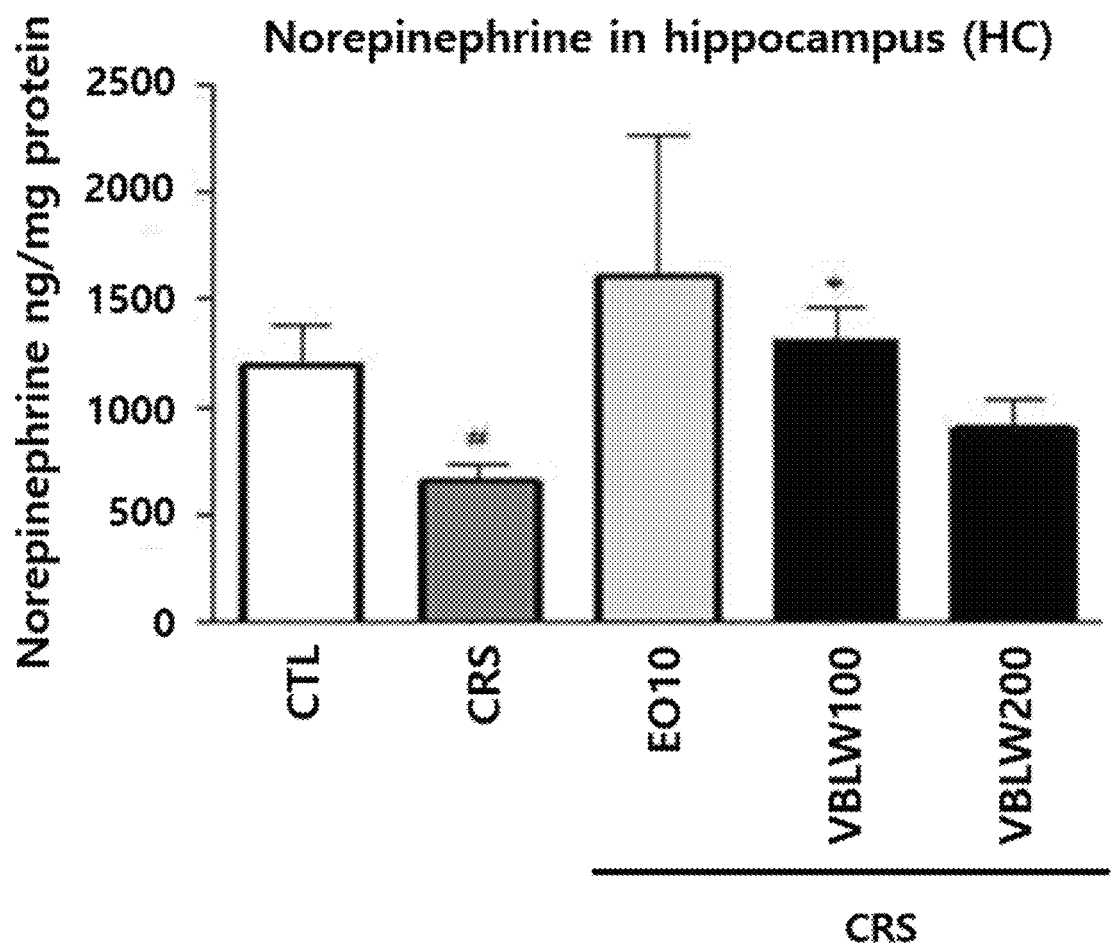
Figure 7C:
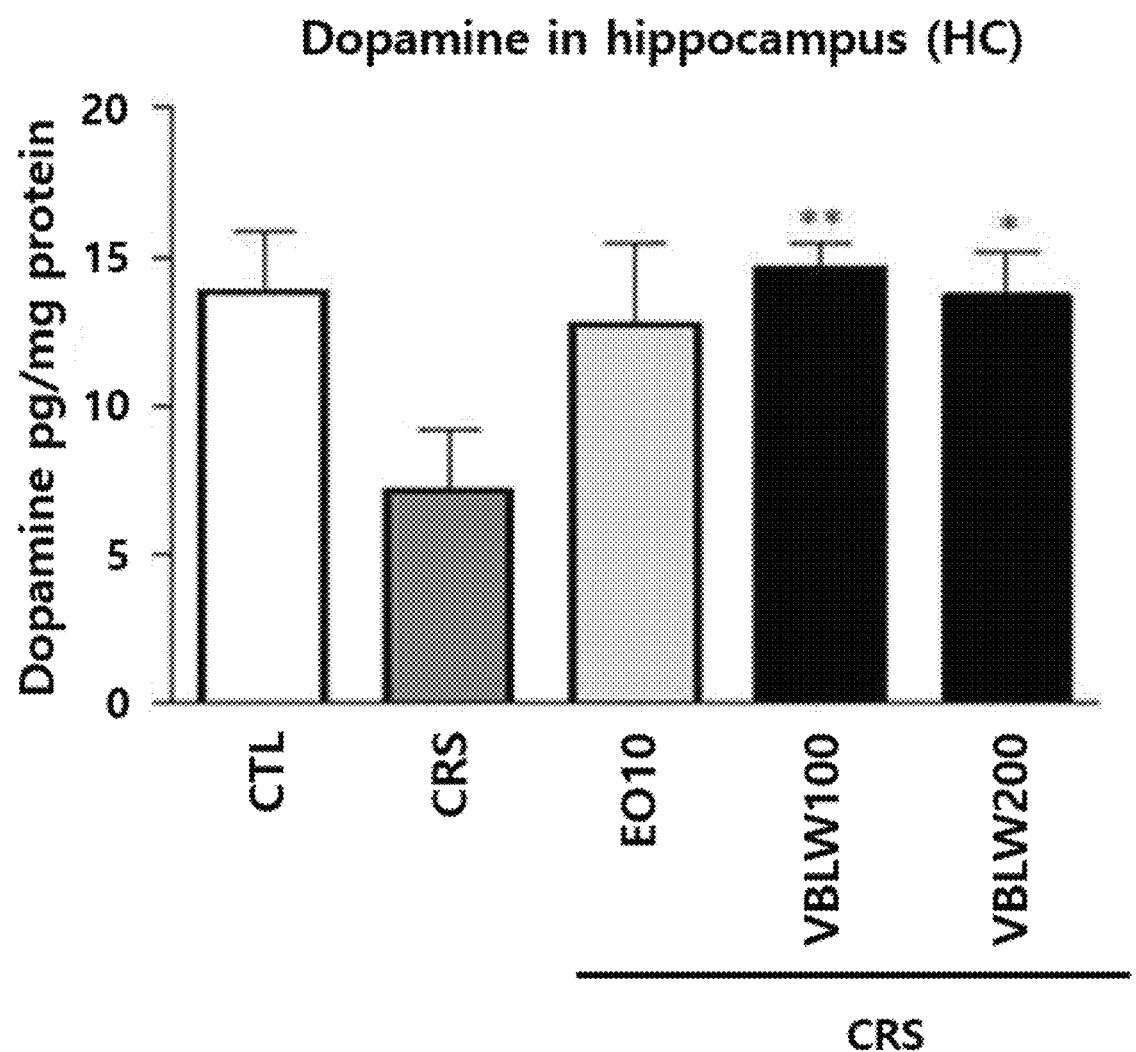
Figure 8A:
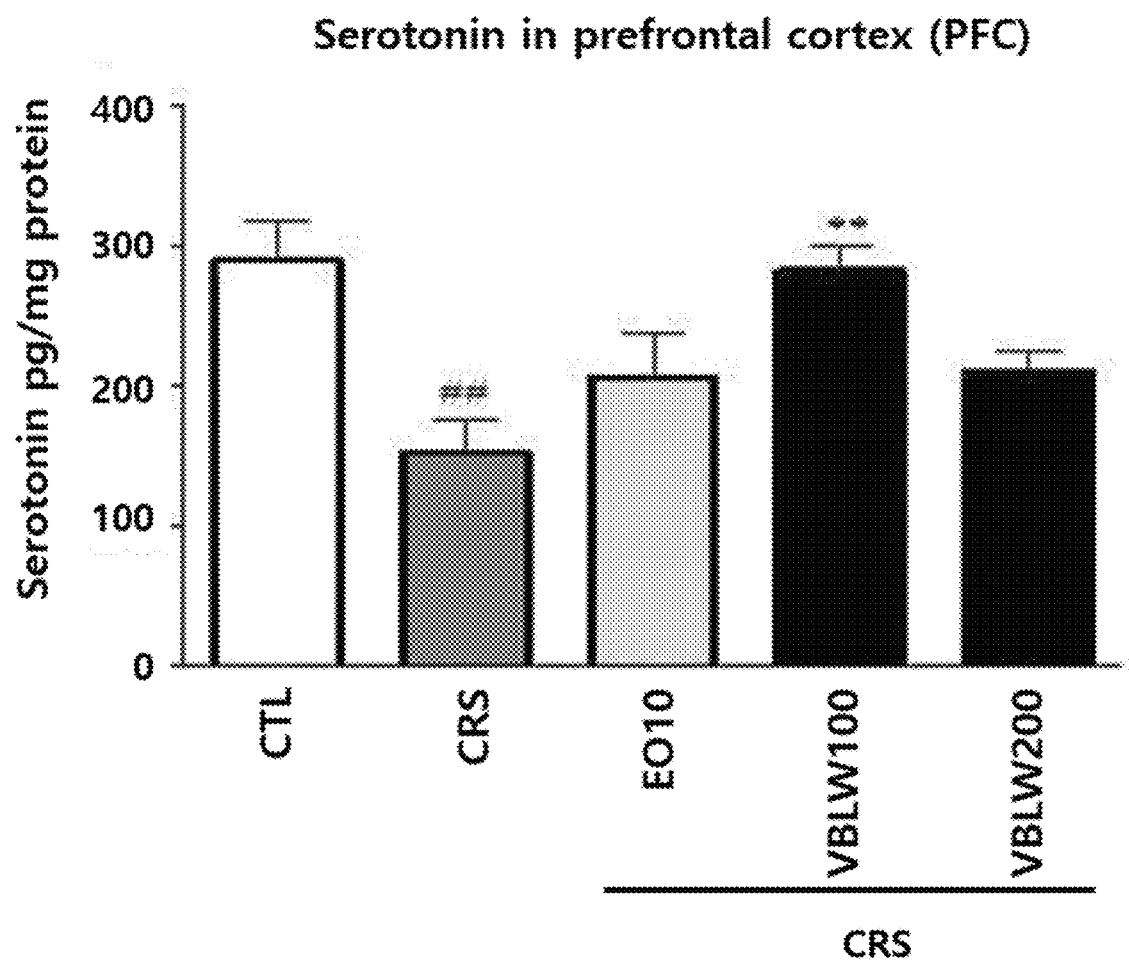
FIGS. 8A, 8B and 8C show effects of the *Vaccinium bracteatum* Thunb. leaf extracts of the present disclosure on the generation of the neurotransmitters serotonin, norepinephrine, and dopamine in the prefrontal cortex (PFC) of chronic restraint stress-induced mice.
Figure 8B:
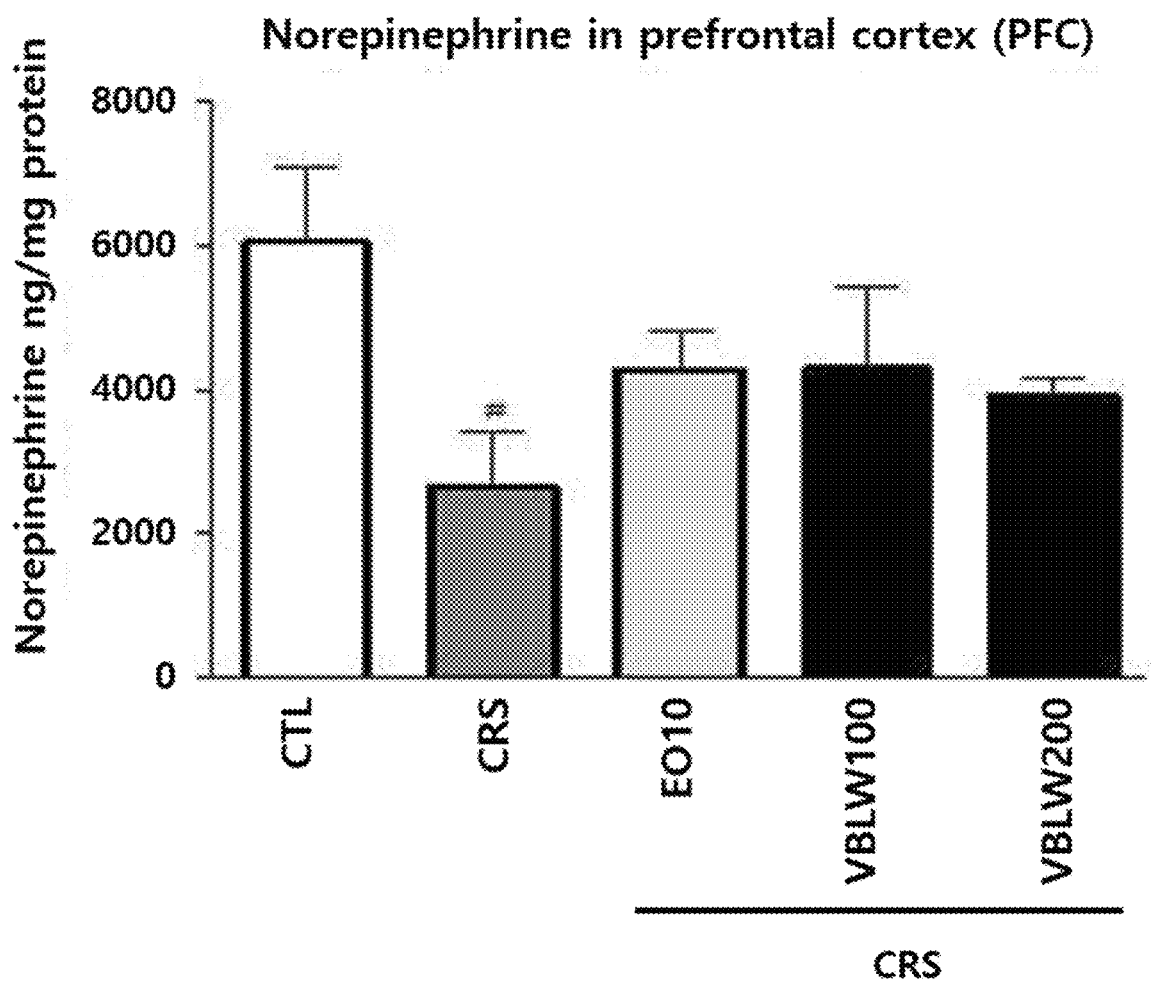
Figure 8C:
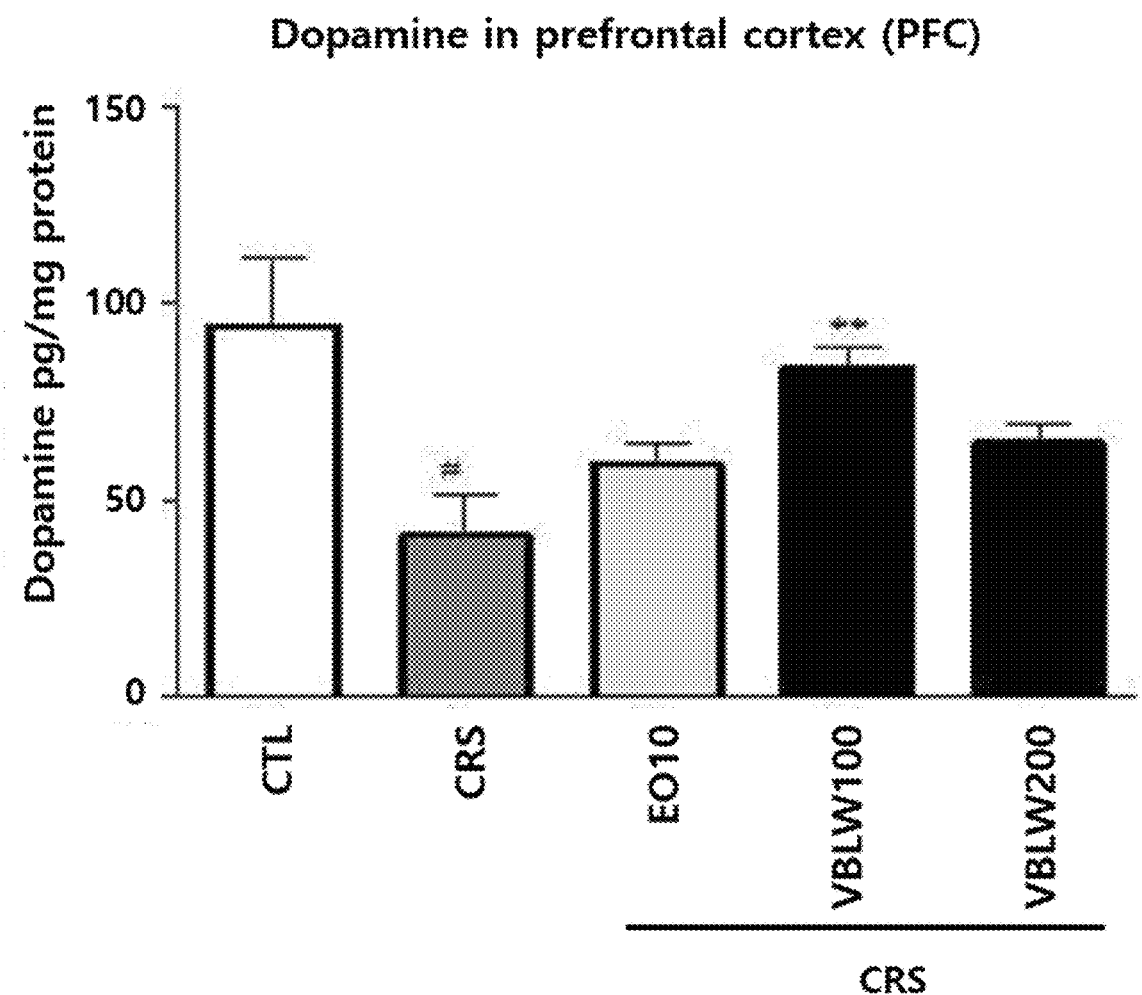

FIGS. 7 and 8 show effects of the *Vaccinium bracteatum* Thunb. leaf extracts of the present disclosure on levels of the neurotransmitters serotonin, norepinephrine, and dopamine in the hippocam pus (HC) and the prefrontal cortex (PFC) of mice having chronic restraint stress induced therein.

As shown in FIG. 7, levels of the neurotransmitters (serotonin, norepinephrine, and dopamine) in the hippocampus were decreased in the restraint stress group (CRS) compared to the control (CTL). Serotonin and norepinephrine levels in the *Vaccinium bracteatum* Thunb. leaf hot-water extract-administered group (VBLW 100 mg/kg p.o) were significantly higher than those in the chronic restraint stress group ($P<0.05$) while the dopamine level was significantly increased in the *Vaccinium bracteatum* Thunb. leaf hot-water extract-administered groups (100 and 200 mg/kg p.o) ($P<0.05$ and $P<0.01$).

As shown in FIG. 8, levels of the neurotransmitters (serotonin, norepinephrine, and dopamine) in the prefrontal cortex of the chronic restraint stress group (CRS) was significantly decreased, compared to the control (CTL) ($P<0.05$ and $P<0.01$). Serotonin and dopamine levels were significantly increased in the *Vaccinium bracteatum* Thunb. leaf hot-water extract-administered group (VBLW 100 mg/kg p.o), compared to the chronic restraint stress group ($P<0.01$). The norepinephrine levels were increased in the *Vaccinium bracteatum* Thunb. leaf hot-water extract-administered groups (VBLW 100 and 200 mg/kg p.o), compared to the chronic restraint stress group, but with no significance.

8. Identification of Stress-Relieving Activity of *Vaccinium bracteatum* Thunb. Leaf Extract in Neuronal Cell SH-SY5Y SH-SY5Y cells (neuroblastoma, human dopaminergic neuronal cells) were incubated in MEM medium containing 1% antimycotics/antibiotics and 10% FBS, seeded at a density of $10^5$ cell/ml on 96-well plates, and then cultured for 24 hours. In order to determine the cytotoxicity of *Vaccinium bracteatum* Thunb. leaf extracts on the neurons, the cells were treated with various concentrations of the extracts. After treatment of the hot-water extracts of *Vaccinium bracteatum* Thunb. leaves for 24 hours, cell viability was measured by MTT assay.

Figure 9A:
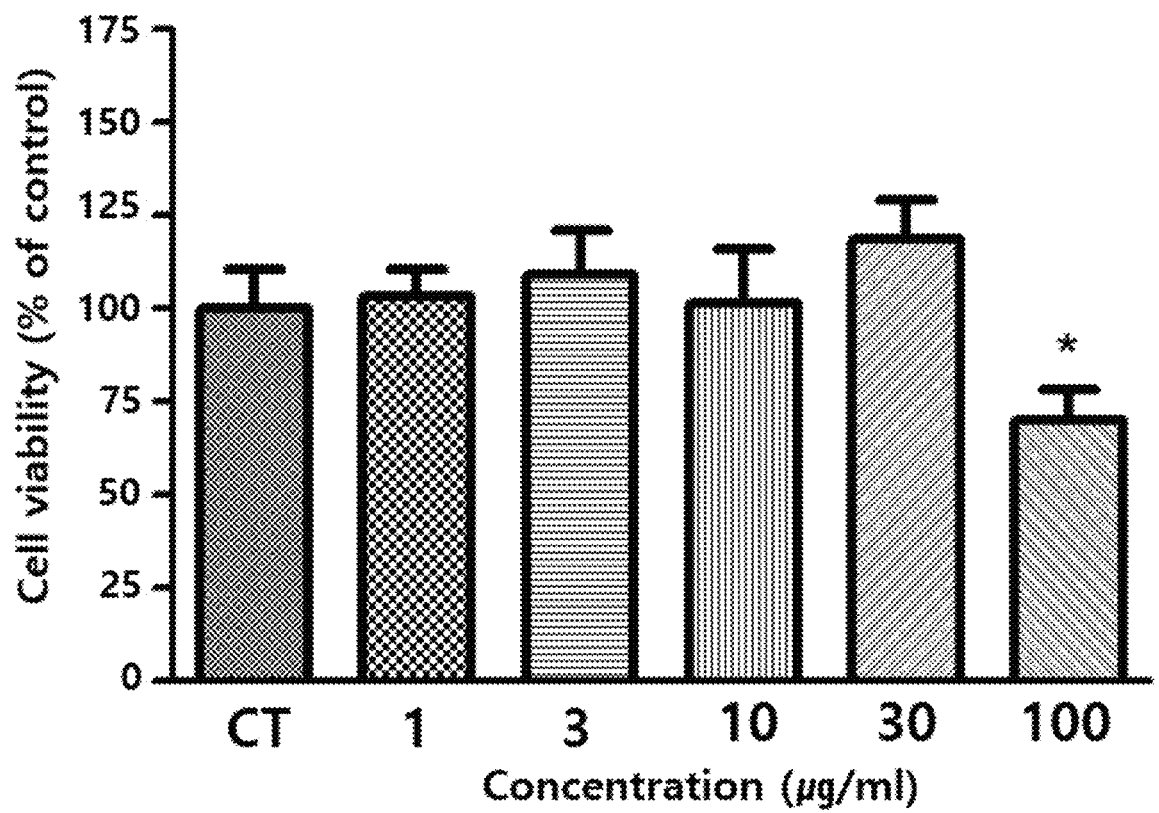
FIGS. 9A and 9B show the cytotoxicity of the *Vaccinium bracteatum* Thunb. leaf extract of the present disclosure against SH-SY5Y cells (neuroblastoma, human dopaminergic neuronal cell) and the neuroprotective activity of the *Vaccinium bracteatum* Thunb. leaf extract against the mental stress hormone corticosterone-induced neuronal damage.

FIG. 9A shows the maximum safety range of the available concentration of the *Vaccinium bracteatum* Thunb. leaf extracts as measured for the cytotoxicity thereof. In this regard, cytotoxicity was measured by applying the hot water extracts of *Vaccinium bracteatum* Thunb. leaves at concentrations of 1, 3, 10, 30, and 100 μg/ml to SH-SY5Y cells. The cell viability was not significantly different between the control (0 μg/ml) and the concentrations of 1, 3, 10, and 30 μg/ml whereas decreasing at the concentration of 100 μg/ml, with significance relative to the control ($P<0.05$). As a result of this experiment, the test was performed within the concentration of 30 μg/ml.

In order to examine the resistance activity of the *Vaccinium bracteatum* Thunb. leaf extracts against mental stress at a cellular level, the extracts were assayed for protective activity against the stress hormone corticosterone-induced neuronal damage. The neuronal cell line SH-SY5Y was treated with various concentrations of corticosterone for 24 hours to determine cytotoxicity. Selection was made of a concentration at which 50-60% of the cells died (data not shown). In the assay for the neuroprotective effect of *Vaccinium bracteatum* Thunb. leaf extracts, the cells were seeded into 96-well microplates and incubated for 24 hours before treatment with the *Vaccinium bracteatum* Thunb. leaf extracts for 2 hours. Again, the cells were incubated for 24 hours with 1 mM corticosterone, followed by an MTT assay for measuring cell viability.

Figure 9B:
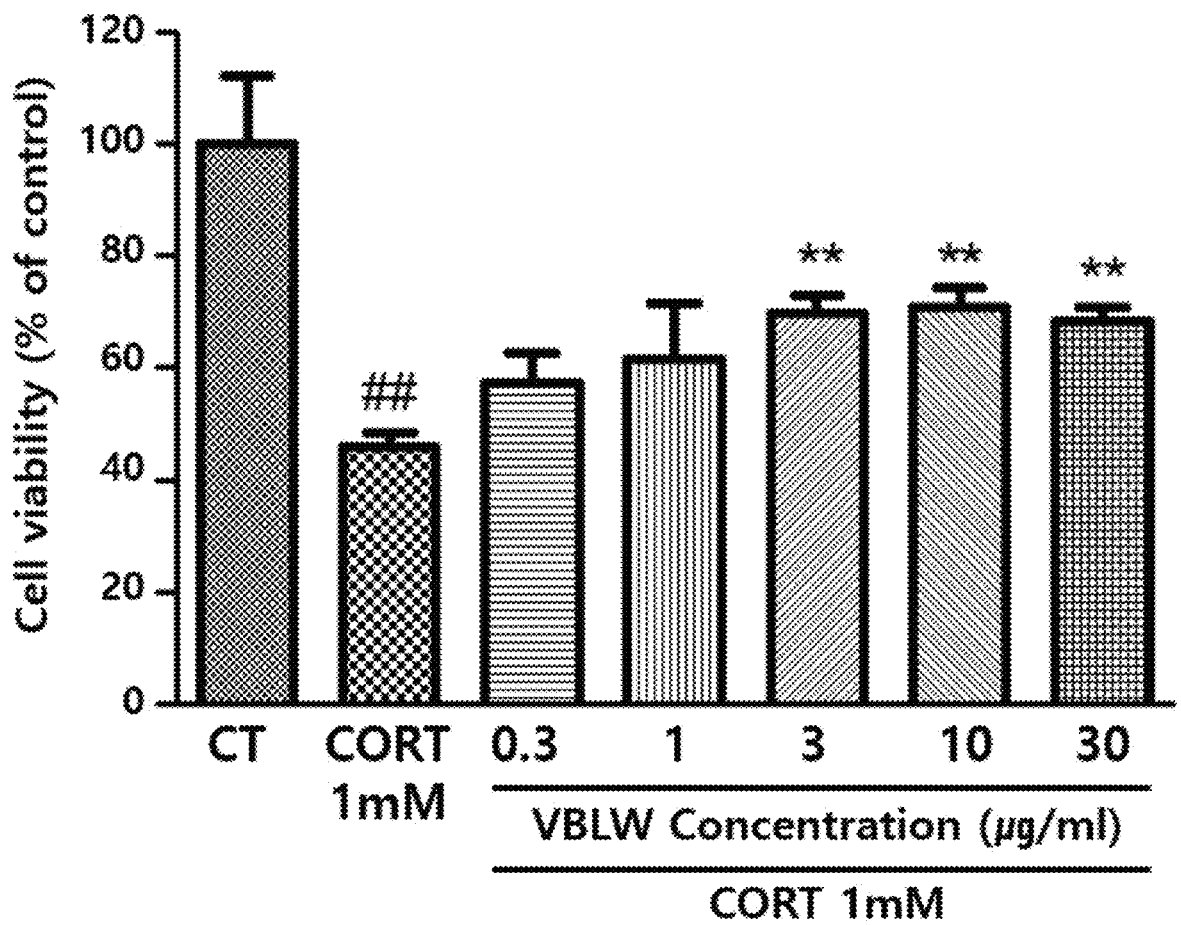

FIG. 9B is a graph showing the neuroprotective activity of *Vaccinium bracteatum* Thunb. leaf extracts against the mental stress hormone corticosterone-induced neuronal damage. In this test, corticosterone was used at the concentration of 1 mM, which accounted for 50-60% cytotoxicity. When the hot-water extracts of *Vaccinium bracteatum* Thunb. leaves were applied at the concentrations of 3, 10, and 30 μg/ml, the cell viability was observed to increase against corticosterone with significance ($P<0.01$).

An experiment was carried out to find out the working signaling pathway responsible for the neuroprotective activity of the *Vaccinium bracteatum* Thunb. leaf extracts against corticosterone-induced neuronal damage. In this experiment, SH-SY5Y cells were pretreated for 1 hour with wortmanin, rapamycin, H89, and PD98059, which are respective pharmacological inhibitors of the PI3K (phosphoinositide 3-kinase), mTOR, PKA (protein kinase A), and MAPK/ERK kinase pathways and then incubated for 2 hours with the hot-water extracts of *Vaccinium bracteatum* Thunb. leaves (3 μg/ml). Thereafter, 24 hours of incubation with corticosterone (1 mM) was followed by measuring cell viability through MTT assay.

Figure 10:
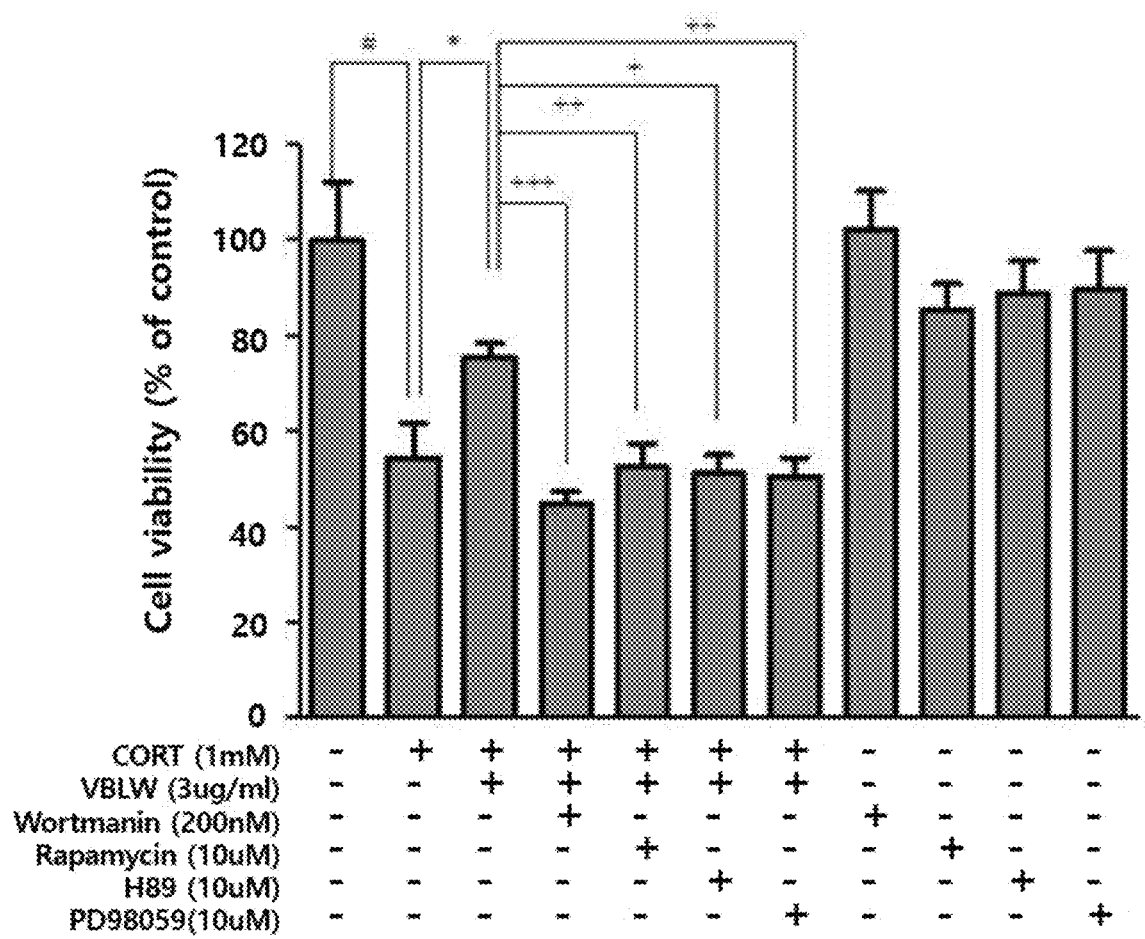
FIG. 10 is a graph showing that the neuroprotective effect of the *Vaccinium bracteatum* Thunb. leaf extract of the present disclosure is exhibited through the PI3K/Akt and PKA/ERK signaling pathways.

FIG. 10 is a graph showing signaling pathways through which the neuroprotective activity of the hot-water extracts of *Vaccinium bracteatum* Thunb. leaves against pharmacological inhibitors of PI3K, mTOR, PKA, and MAPK/ERK kinase (MEK).

For use in the experiment, the inhibitors alone were assayed for cytotoxicity. No cytotoxicity was observed in 24-hour incubation with the mTOR inhibitor (rapamycin), the PKA inhibitor (H89), or the MAPK/ERK kinase (MEK) inhibitor (PD98059), but except for the PI3K inhibitor (wortmanin). Compared to the corticosterone-treated group (54.45±4.04%), a protective effect of 75.21±1.75% was detected in the group treated with 3 μg/ml of the hot-water extract of *Vaccinium bracteatum* Thunb. leaves (VBLW) ($P<0.05$). When comparison was made between the groups treated with corticosterone and the hot-water extract of *Vaccinium bracteatum* Thunb. leaves and the groups treated with corticosterone and the hot-water extract of *Vaccinium bracteatum* Thunb. leaves plus the pharmacological inhibitors, significant neuroprotective effects were observed in the PI3K inhibitor (44.84±1.40%, P<0.001), the mTOR inhibitor (52.46±2.82%, P<0.01), the PKA inhibitor (51.08±2.27%, P<0.05), and the MEK inhibitor (50.34±2.31%, P<0.01).

Therefore, these results indicate that the hot-water extracts of *Vaccinium bracteatum* Thunb. leaves exhibit neuroprotective activity against corticosterone-induced cell damage through the PI3K/AKT and PKA/ERK signaling pathways.

9. Effect of *Vaccinium bracteatum* Thunb. Leaf Extract on Cyclic AMP Activity of 5-HT$_6$ Receptor-Expressing Cell Line For use in the experiment, human astrocytoma 1321N1 cells that stably expressed the human serotonin 5-HT$_6$ receptor gene were purchased from Perkin Elmer and grown for 24 hours. Then, the supernatant medium was aspirated and changed with 1∓ PBS containing the phosphodiesterase inhibitors IBMX (0.5 mM) and Ro 20-1724 (0.1 mM) before the cells were treated for 30 minutes with various concentrations of the hot-water extracts of *Vaccinium bracteatum* Thunb. leaves. Cell lysates were obtained from the cultures and measured for cyclic AMP levels (samples with drug alone). Separately, the cells were treated for 15 minutes with *Vaccinium bracteatum* Thunb. leaf extracts and then for 15 minutes with 100 μM of 5-HT. The resulting cell lysates (drug pre-treated sample, drug+5-HT) were measured for cAMP levels, using the R&D Systems cAMP Assay kit according to the manufacturer's instructions.

Figure 11A:
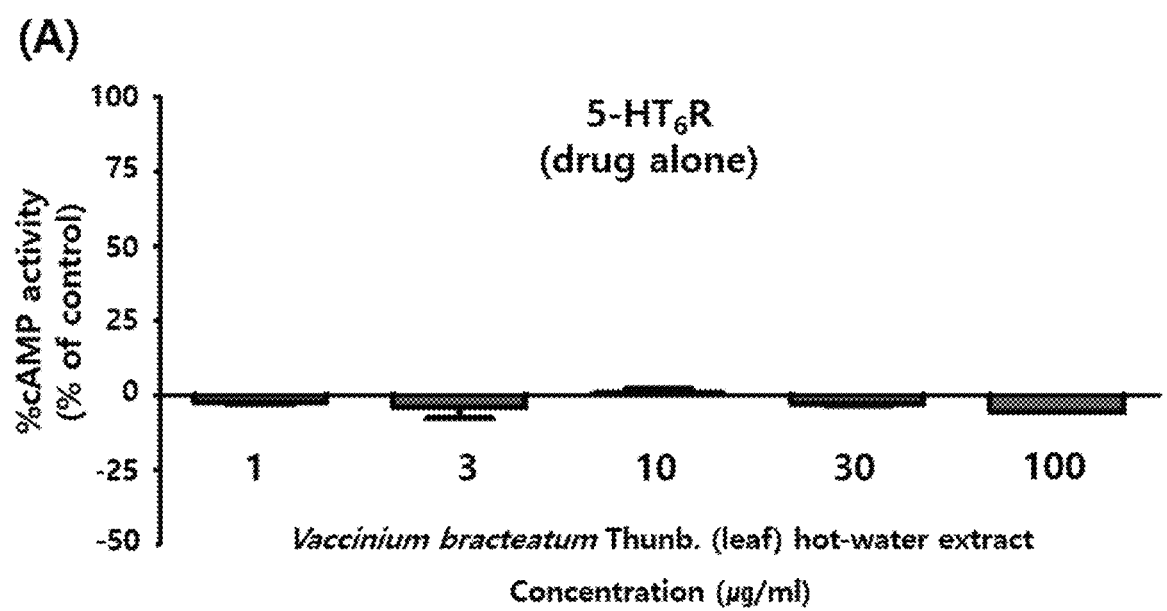
FIGS. 11A and 11B show inhibitory activity of the *Vaccinium bracteatum* Thunb. leaf extract of the present disclosure against 5-HT-induced intracellular cAMP increase in a 5-HT$_6$ receptor gene-expressing cell line.
Figure 11B:
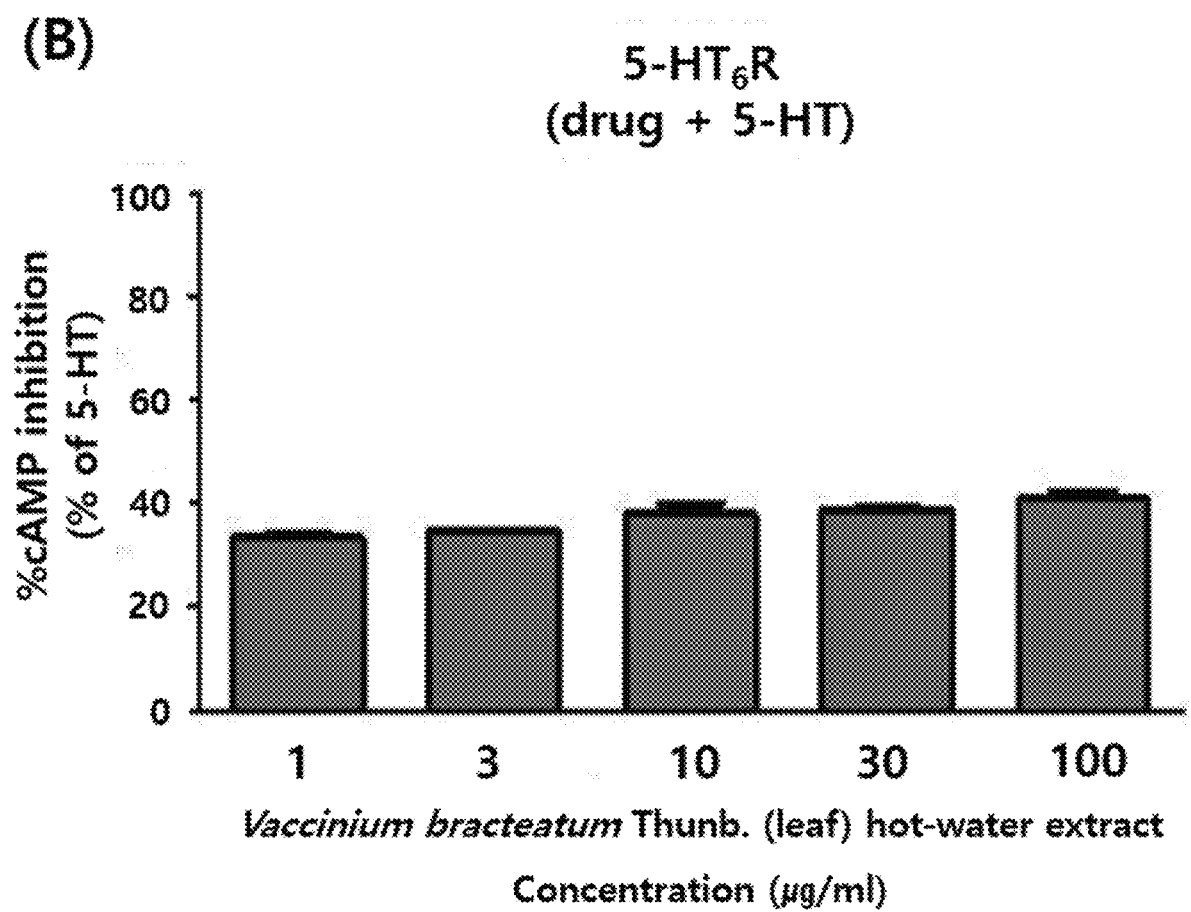

As shown in FIG. 11, the hot-water extract of *Vaccinium bracteatum* Thunb. leaves alone did not affect the cyclic AMP activity. The results obtained in the application of 5-HT for 15 minutes after 15-min pretreatment with various concentrations of the hot-water extract were calculated assuming that the cAMP activity was 0 (zero) upon the 15-min pretreatment with 5-HT (100 μM) alone. The hot-water extract of *Vaccinium bracteatum* Thunb. leaves exhibited an antagonistic effect on the 5-HT$_6$ receptor, which mediates cyclic AMP activity.

10. Effect of *Vaccinium bracteatum* Thunb. Leaf Extract on Intracellular Ca$^{2+}$ Activity in Cell Line Expressing 5-HT$_{2A}$ Receptor Gene The CHO-K1 cell line (Chinese hamster ovary cells) was purchased from ATCC and seeded into 96-well plates (black wall/clear bottom, BD Falcon) containing a medium (RPMI 1640, fetal bovine serum 10%, penicillin 100 IU/ml, streptomycin 100 μg/ml) before incubation at 37° C. for 24 hours in a 5% CO$_2$ incubator. A serotonin 2A receptor (5-HT$_{2A}$ receptor) cDNA was transiently expressed for 48 hours in the cells with the aid of the plasmid transfection reagent Lipofectamine 2000. The cells were washed once with HEPES-buffered solution (155 mM NaCl, 2 mM CaCl$_2$, 1 mM MgCl$_2$, 3 mM KCl, 10 mM HEPES, 10 mM Glucose, pH 7.4) before fluorescent staining was conducted by applying the fluorescent dye Fura-2/AM at a final concentration of 5 μM to the cells and incubating the cells at 37° C. for 60 min in a 5% CO$_2$ incubator under a light-shielded condition. Then, the cells were washed once with a HEPES-buffered solution. For intracellular calcium imaging, the cells were selectively exposed to 340/380 nm light radiations using a high-throughput system (HTS) system. The 340/380 nm ratios were calculated using a digital fluorescence analyzer. Because Ca$^{2+}$-bound Fura-2/AM within cells is excited at 340 nm while free Fura-2/AM is excited at 380 nm, an increased 340/380 nm ratio means abundance of Ca$^{2+}$-bound fura-2/AM within the cells.

Intracellular calcium levels were measured in the cells treated with 100 μM of 5-HT after 1-min pretreatment with the hot-water extract of *Vaccinium bracteatum* Thunb. leaves at concentrations of 1, 3, 10, 30, and 100 μg/ml while the value obtained from treatment with 100 μM of serotonin (5-HT) without the pretreatment was set as a control. For reference, the numerals shown on the error bars of FIG. 12 for individual items indicate cell counts used in the experiments.

Figure 12:
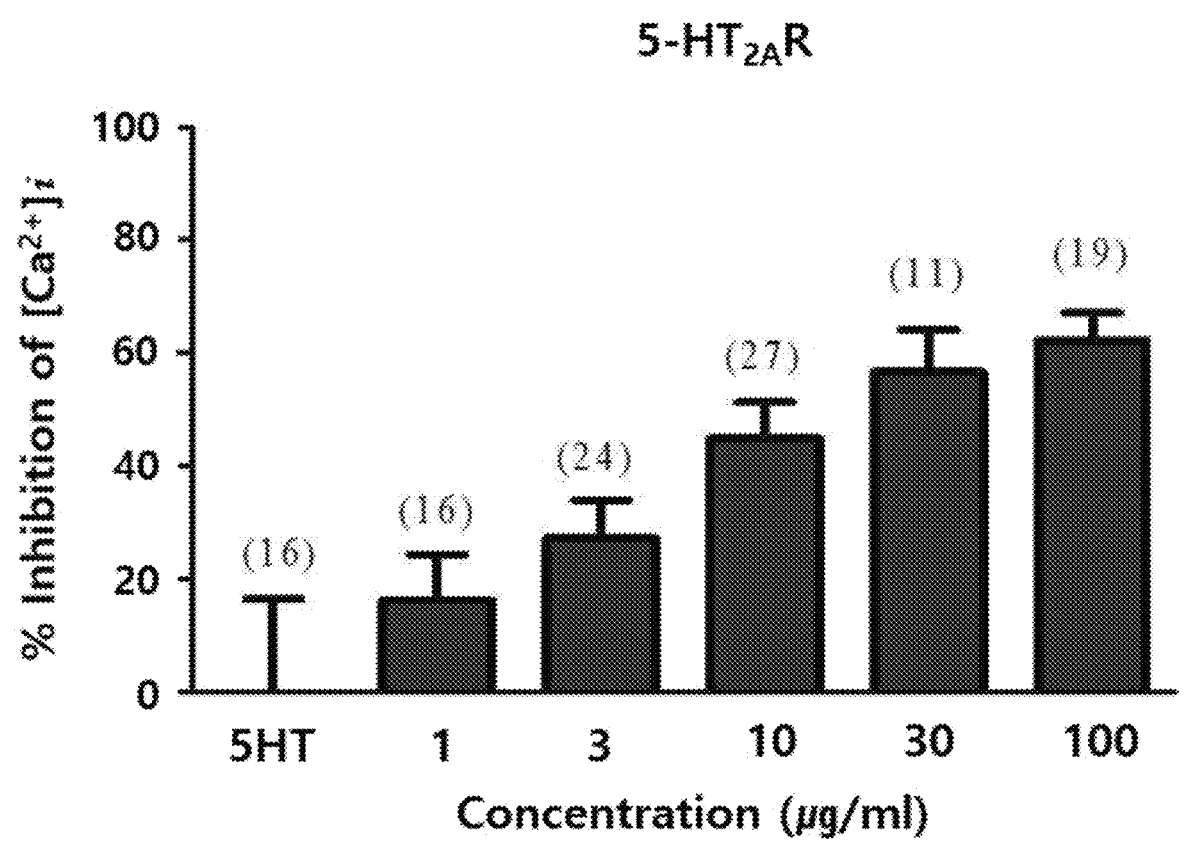
FIG. 12 is a graph showing the inhibitory effect of the *Vaccinium bracteatum* Thunb. leaf extract of the present disclosure on 5-HT induced intracellular Ca$^{2+}$ increase in a 5-HT$_{2A}$ receptor gene-expressing cell line.

FIG. 12 is a graph showing the dose-dependent inhibition effect of the hot-water extract of *Vaccinium bracteatum* Thunb. leaves of the present disclosure on 5-HT induced intracellular Ca$^{2+}$ increase in a cell line expressing a 5-HT$_{2A}$ receptor gene. The hot-water extract of *Vaccinium bracteatum* Thunb. leaves inhibited the 5-HT-induced intracellular Ca$^{2+}$ increase which is mediated by the 5-HT$_{2A}$ receptor, compared to 5-HT, thus exhibiting an antagonistic effect on the 5-HT$_{2A}$ receptor. As shown in FIG. 12, when used at 1, 3, 10, 30, and 100 μg/ml, the hot-water extract of *Vaccinium bracteatum* Thunb. leaves inhibited 5-HT$_{2A}$ receptor-specific serotonin-induced intracellular Ca$^{2+}$ accumulation by 16.23±2.03%, 27.33±1.35%, 45.00±1.22%, 56.73±2.23%, and 62.31±1.10%, respectively, compared to the control (5-HT, 100 μM).

11. Preparation of Medicine or Health Food Using *Vaccinium bracteatum* Thunb. Leaf Extract A pharmaceutical composition comprising a *Vaccinium bracteatum* Thunb. leaf extract as an effective ingredient for prevention or treatment of stress-related disease and depression may be prepared in the form of a tablet, a capsule, a soft capsule, an granule, or a liquid agent. According to another appropriate embodiment, the composition may be prepared into a beverage additive. The medicament or the health food for the prevention or treatment of stress disorder and depression may be formulated into a powder, a granule, a tablet, a capsule, a suspension, an emulsion, a syrup, an aerosol, a transdermal preparation, a suppository, or a sterile injectable solution, with the composition comprising the *Vaccinium bracteatum* Thunb. leaf extract as an effective ingredient contained in an amount of 0.01 to 99.9 wt % therein.

For a sterile injection solution, the pharmaceutical composition may be used in an amount of 0.01 to 99.9 wt. %, together with the balance amount from 99.9 to 0.01 wt % of corresponding amount of purified water or glucose A capsule may comprise 0.01 to 99.9 wt. % of the pharmaceutical composition lyophilized, together with the balance from 99.9 to 0.01 wt. % of a vitamin and/or calcium.

The pharmaceutical composition thus prepared may be daily administered at a dose corresponding to 100-200 mg of the extract per kg of both weight. In addition, the pharmaceutical composition may be contained in an amount of 0.01 to 99.9 wt. % in a functional health food for prevention or treatment of stress-related disease and depression.

INDUSTRIAL APPLICABILITY

The present invention provides a pharmaceutical composition comprising a *Vaccinium bracteatum* Thunb. leaf extract as an effective ingredient for prevention or treatment of stress-related disease and depression. By employing the plant inhabiting in nature as a raw material, the present invention can reduce the production cost and is expected for import substitution and export effects through industrialization. Therefore, the present invention is industrially available.

What is claimed is:

1. A method for treatment of stress-related anxiety comprising:
   administering to a subject in need thereof a composition containing a therapeutically effective amount of a *Vaccinium bracteatum* Thunb. leaf extract,
   wherein the *Vaccinium bracteatum* Thunb. leaf extract is obtained using a solvent consisting of water.

2. The method of claim 1, wherein the *Vaccinium bracteatum* Thunb. leaf extract is comprised at a daily dose of 100 to 200 mg per kg of body weight.

3. The method of claim 1, wherein the composition is in a form of a tablet, a capsule, a granule, or a liquid preparation.

* * * * *